United States Patent [19]

Janssen et al.

[11] Patent Number: 5,038,371
[45] Date of Patent: Aug. 6, 1991

[54] X-RAY EXAMINATION APPARATUS HAVING THREE AXES OF ROTATION

[75] Inventors: Jozef T. A. Janssen; Robert van der Ploeg; Cornelis L. Schuppert; Adrianus A. J. van der Vegt, all of Eindhoven, Netherlands

[73] Assignee: U.S. Philips Corporation, New York, N.Y.

[21] Appl. No.: 550,248

[22] Filed: Jul. 6, 1990

Related U.S. Application Data

[63] Continuation of Ser. No. 322,747, Mar. 13, 1989, abandoned.

[30] Foreign Application Priority Data

Mar. 14, 1988 [NL] Netherlands ............... 8800614

[51] Int. Cl.5 .................... H05G 1/02; A61B 6/00
[52] U.S. Cl. ................... 378/197; 378/193; 378/196; 378/195; 378/4
[58] Field of Search ............ 378/25, 24, 39, 195, 378/196, 197, 198, 180, 4, 193

[56] References Cited

U.S. PATENT DOCUMENTS

| 3,281,598 | 11/1966 | Hollstein | 250/57 |
| 3,892,967 | 7/1975 | Grady | 250/447 |
| 4,071,769 | 1/1989 | Brunnett et al. | 378/197 |
| 4,481,656 | 11/1984 | Janssen et al. | 378/196 |
| 4,653,083 | 3/1987 | Rossi | 378/195 |

FOREIGN PATENT DOCUMENTS 2108657 9/1971 Fed. Rep. of Germany .

Primary Examiner—Edward P. Westin
Assistant Examiner—Don Wong
Attorney, Agent, or Firm—William Squire

[57] ABSTRACT

An x-ray examination apparatus in which an opposed x-ray source and x-ray image detector, which establish a radiation vector and an image orientation direction traverse to said vector, are mounted to be positioned relative to a series of three independently operable axes of rotation. Computing and measuring means are provided by which angular positions of rotation about the various axes can be correlated to simultaneously achieve both a desired angular orientation of the radiation vector and a desired direction of image orientation.

11 Claims, 2 Drawing Sheets ns a patient to be examined is
X-RAY EXAMINATION APPARATUS HAVING THREE AXES OF ROTATION This is a continuation of application Ser. No. 322,747, filed Mar. 13, 1989, abandoned.

BACKGROUND OF THE INVENTION

1. Field of the Invention

The invention relates to an X-ray examination apparatus comprising an X-ray source and an X-ray detector which are accommodated at some distance diametrically with respect to each other and can be rotated collectively about three axes relative to a table which can be moved between the X-ray source and the X-ray detector, which axes define a first system of coordinates and in which means are incorporated to determine a radiation vector along a central beam which connects the X-ray source and The X-ray detector, of which radiation vector a base is drawn by vectors situated along the axes of the first system of coordinates. Of interest is co-pending application Ser. No. 370,213, filed June 6, 1989, entitled "X-Ray Examination Apparatus Comprising Balanced Supporting Arm" in the name of Endschot et al and assigned to assignee of the present invention.

2. Description of the Prior Art

Such an X-ray examination apparatus is disclosed in U.S. No. 3,281,598. In an apparatus described in said specification the axes of rotation are realised by suspending the X-ray tube and the X-ray detector in a C-arm which is rotatable in the plane of the C-arm about a first axis. The C-arm is further connected to a support so as to be rotatable about a second axis, the support being connected to the ceiling so as to rotate about a vertical axis. The apparatus is isocentric, which means that the three axes have a common point of intersection, the isocentre. The isocentre customarily lies in an object to be examined.

The large freedom of movement of the system X-ray source-X-ray detector, hereinafter briefly referred to as the image-forming system, has many advantages. As a matter of fact, a patient can now be radiated under a great variety of directions. This is of great use, for example, for catheterisation.

German Patent Specification DE No. 21 08 657 discloses an X-ray examination apparatus in which a C-arm supports an X-ray source and an X-ray detector. Transducers to determine the position of the radiation vector are connected to the X-ray examination apparatus. By radiating an object in two mutually perpendicular directions, two projection images are obtained which are displayed on a television monitor, the signal values generated by the transducers which are also proportional to the angles of rotation of the C-arm being stored in a computing unit. An image line can be selected electronically in the two monitor images. A projection of the selected line can be computed for all the positions of the radiation vector which are measured by the transducers and be displayed in the X-ray image. For example surgery may take place along the selected line.

In use the known apparatus has as a disturbing drawback in that the orientation of a radiation image, for example, displayed on a monitor, rotates. The radiologist loses much time to be able to interpret the displayed image anatomically and the possibility of a wrong diagnosis increases. Further the freedom of movement of the operating personnel near a patient to be examined is strongly restricted.

SUMMARY OF THE INVENTION

It is the object of the invention to avoid this drawback and for that purpose an X-ray examination apparatus of the type mentioned in the opening paragraph is characterized according to the invention in that computing means are also incorporated to determine the radiation vector with respect to a base which is drawn by vectors situated along the axes of a second system of coordinates which is rotated with respect to the first system of coordinates.

Since in an apparatus according to the invention means are incorporated to determine the radiation vector with respect to a system of coordinates to be chosen freely, the movement of the X-ray source and the X-ray detector can be controlled so that one of the axes of the second system of coordinates coincides with, for example, the longitudinal axis of a patient. It is also possible, for example, to orient one of the axes so as to always coincide with a recognisable axis through an object, for example the spinal column, but also the direction of a blood vessel to be displayed. Image rotation on the monitor of the object to be displayed is prevented by this.

In a preferred embodiment the computing means produce coupled movements for realising a previously adjusted series of orientation radiographs. The control is carried out so, for example, that there is proceeded from a previous to a subsequent direction of radiation with a minimum of angular rotations. In a partly manually operated apparatus the use of a light view may also be considered for this purpose. By projecting from a light view a gap image on an object to be examined and combining a given orientation of a gap image with a given angular orientation for radiography, a desired image can be realised on the monitor.

In a further preferred embodiment the X-ray source and an X-ray image intensifier are mounted on a C-arm in such a manner that a rotation about an axis transversely to the plane of the C-arm can extend over at least twice 90°. Therefore the C-arm can slide beyond the X-ray tube or the X-ray image intensifier tube, or both, through a C-arc base. For this purpose, in particular the C-arm is constructed to be so wide that the X-ray tube and the X-ray intensifier tube can be mounted therein without laterally projecting parts. Such a C-arm may also be extended to form a complete ring and, for example, may be provided for bi-plane examinations with 2 X-ray sources and 2 image intensifier tubes.

In a further embodiment an X-ray source and an X-ray image intensifier tube are mounted in a common support in such a manner that this assembly is fully balanced with respect to a common point of gravity which preferably lies in or near the isocentre, for which purpose counterpoises are added to the X-ray source of the detector. Counterpoises are necessary in particular, for example, when the detector can be moved in the direction of the radiation vector, which is the major beam of an X-ray beam emitted by the X-ray source and captured by the detector. For each re-orientation the detector, for example, will first be provided in a balanced position. For the re-orientation itself no gravities need be overcome. Without a radial movability of the detector in the C-arm the image-forming system is always balanced.

A few preferred embodiment according to the invention will now be described in greater detail with reference to the drawing, in which:

DETAILED DESCRIPTION OF THE PREFERRED EMBODIMENTS

Figure 1:
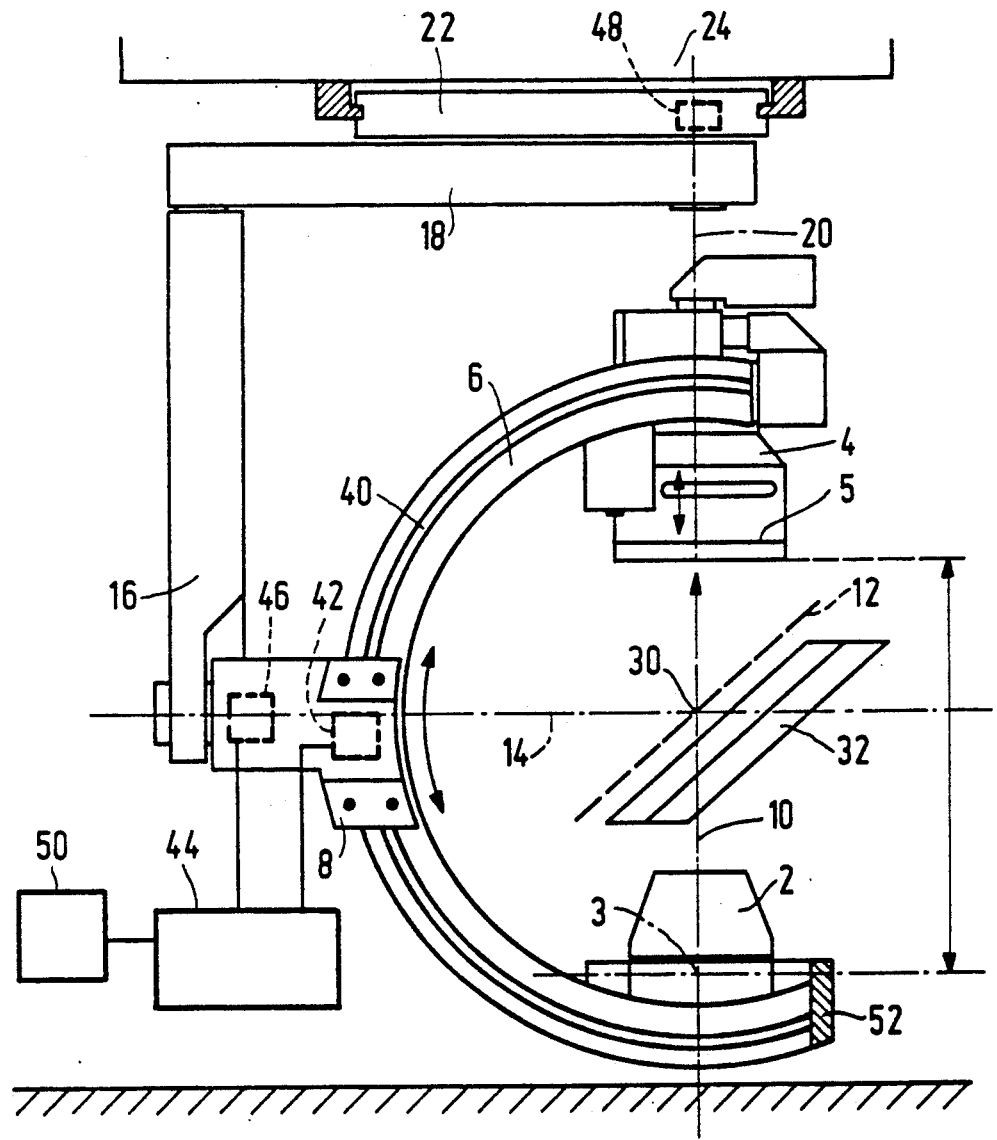
FIG. 1 shows diagrammatically an apparatus according to the invention constructed as a ceiling apparatus having a C-arm construction.

An X-ray examination apparatus as shown in FIG. 1 comprises an X-ray source 2 having a radiation object focus 3 and a detector comprising X-ray image intensifier 4 with an input screen 5. The focus 3 and the screen 5 are mounted at a mutual distance L in a C-arm 6. The C-arm is mounted in a C-arm base 8 so as to be movable. By moving the C-arm 6 through the base 8, the system comprising the X-ray source 2 and the X-ray detector formed by intensifier 4 and screen 5 and hence a radiation vector 10 performs, as already noted, a rotation about an axis 12 which in this case is transverse to the plane of the drawing coinciding with a major beam of an X-ray beam to be emitted by the X-ray source and to be captured by the X-ray detector. (For clarity the axis is shown differently, as if in an isometric format namely not by means of a single spot, for an axis normal to the plane of the drawing but by a dashed line.)

The C-arm base 8 is connected so a supporting arm 16 to as to be rotatable about an axis 144. The supporting arm 16 is connected to a supporting beam 18 which is connected to a supporting plate 22 so as to be rotatable about an axis 20. The supporting plate 22 is connected, for example, via an X-Y translation system, to only an X-translation system or is connected entirely rigidly to a ceiling 24. The construction is isocentric if the axes 12, 14 and 20, as shown, have a common point of intersection 30. For this purpose, an adapted supporting plate 22 having an X-Y translation mechanism may be used for the axis 20. The point of intersection 30 is customarily termed the isocentre and preferably lies in an object to be examined. As regards the X-ray image intensifier 4 for picture display on a monitor it often comprises a television camera tube on an output side.

For capturing signals which are a measure of angular rotations about different axes the C-arm is equipped with a measuring rule 40 and a measuring device 42 is incorporated in the base 8 which records movement of the C-arm with respect to, for example, a zero reference position, for example, the vertical position shown, and transfers it as an electric signal to a control device 44.

Figure 2A:
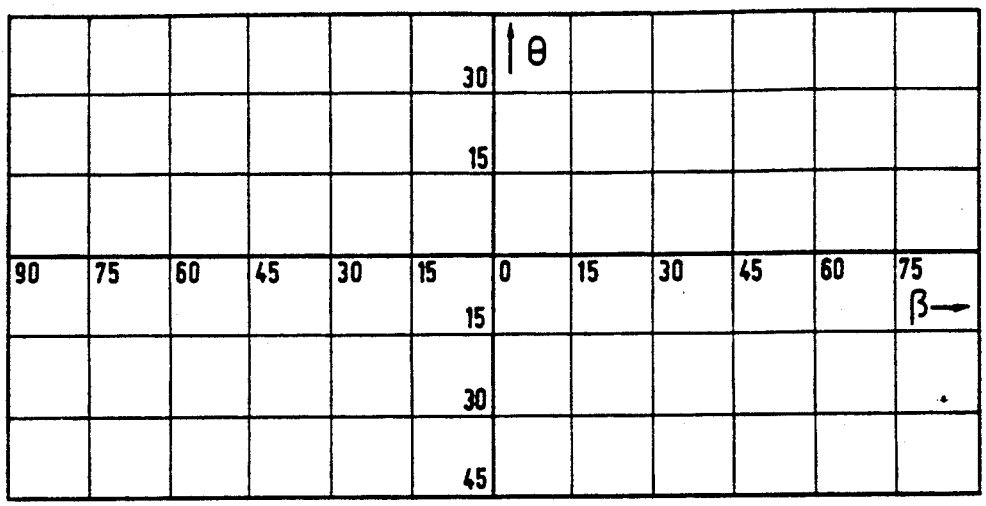
FIGS. 2a, b and c are charts which show different paths of the X-ray detection.
Figure 2B:
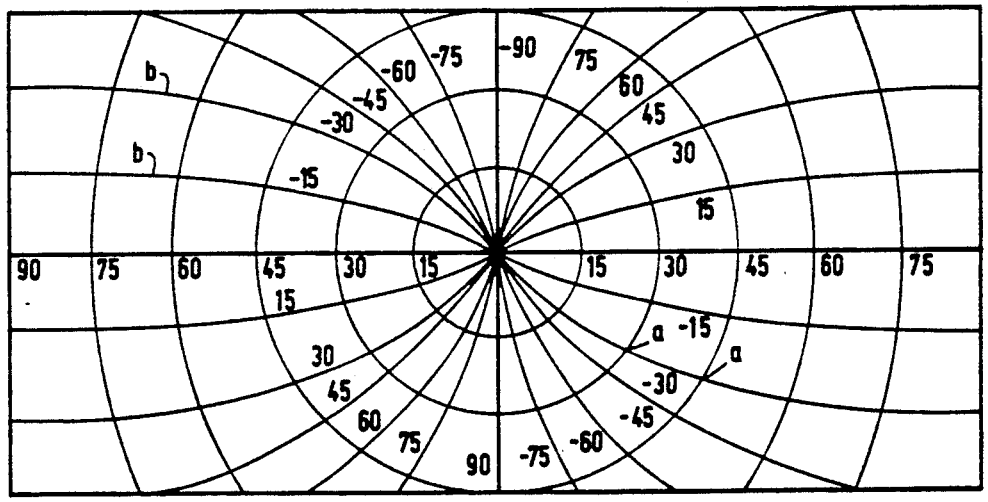
Figure 2C:
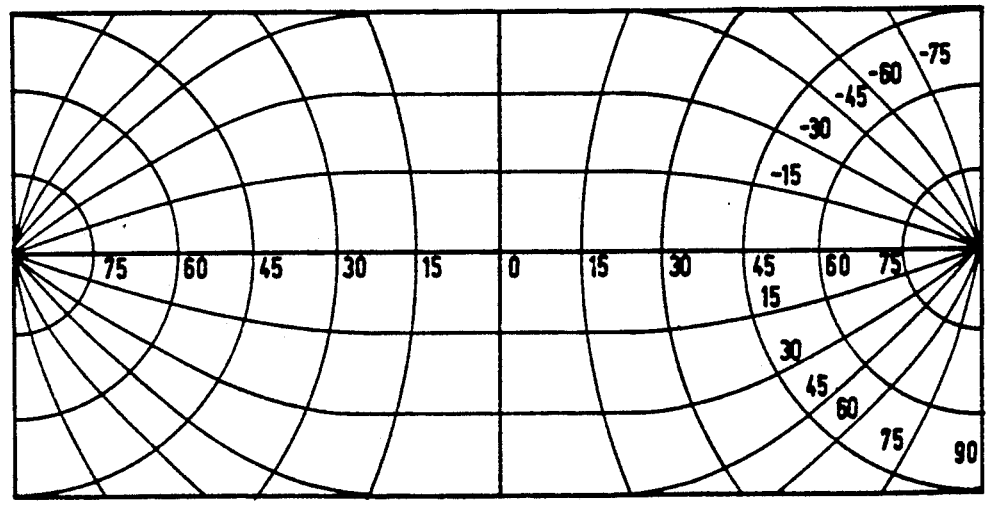

For measuring positions of rotation of the two other axes 14 and 20 angular measuring devices 46 and 48 may be incorporated for example, in the form of encoders. For making different projections of an object the X-ray detector intensifier 4 must be movable on an imaginary hemisphere over a first reference object to be examined. The X-ray detector intensifier 4 is moved by moving the C-arm 6 through the base 8 and by rotation of the base 8 about the axis 14. The angle $\theta$ through which the C-arm 6 is rotated about axis 12 relative to the base 8 and the angle $\beta$ through which the base is rotated about the axis 14 define the position of the radiation vector 10 with respect to the system of coordinates formed by the axes 12, 14 and 20. When an object lies with its axis along the axis 14, the orientation of the object in the image to be radiographed does not vary. By adjusting the angles $\theta$ and $\beta$ the X-ray detector intensifier 4 covers a path over the hemisphere considered above the object a flat projection of which is shown in FIG. 2a. If an object does not lie along the axis 14 it will be necessary for a constant orientation of the object in a radiograph to move the radiation vector with respect to a new second reference system of coordinates an axis of which lies along the axis of the object. This new system of coordinates with axes 12', 14' and 20' is rotated with respect to the first system of coordinates. In order to cause the radiation vector to cover a path which with respect to the new system of coordinates corresponds to the projection shown in FIG. 2a, the angles $\theta$ and $\beta$ will have to vary collectively. FIG. 2b shows the angles $\theta$ and $\beta$ for movements of the radiation vector with respect to a system of coordinates which is formed by rotating the axes 14, and 20 through 90° about the axis 12. For rotation of the radiation vector 10 about the axis 14' the X-ray detector intensifier 4 moves in the plane of projection of the hemisphere along the circular paths a in FIG. 2b, while for the rotation of the radiation vector about the axis 12' the X-ray detector intensifier 4 moves along the paths b. FIG. 2c shows the angles $\theta$ and $\beta$ for movements of the radiation vector 10 with respect to a system of coordinates that is formed by rotating through 180° about the axis 12. Measured signals from the measuring device can also be applied to the control device 44. The control device 44 controls the X-ray detector intensifier 4 along paths, for example a or b as shown in FIG. 2b and 2c, for a rotation of the radiation vector through angles $\theta$ and $\beta$ with respect to a system of coordinates to be chosen freely. So in the control device 44 the radiation vector is determined with respect to a second reference coordinate system to be chosen freely. For the recording of angular orientations it is irrelevant whether the rotations are performed manually or by means of motors. On the other hand, in the case of a motor driven construction the orientation may be carried out, for example, by counting steps of a stepping motor or by the addition of an encoder to a linear motor. In this case also it may be desirable for image orientation that orientation signals are transmitted to the control device 44. For further automation a reading memory device 50 may be added to the control device. By means of this the control device can be actuated from an information carrier or by means of only a function button control to perform a desired measuring program. For a predetermined radiographing program the number of angular rotations of the C-arm and the base 8 can be minimized by the correct choice of the system of coordinates. For a more detailed description of such control mechanisms reference may be made, for example to U.S. No. 4,481,656.

In another construction a light projector is preferably connected on the detector. The projector, for example, forms a line image on an object to be examined or on a patient-table 32 therefor. A given orientation thereof corresponds to a given radiographic orientation and hence to a picture orientation on a display device. In particular, in a manually operated apparatus, this construction works favourably because the examiner only needs to bring the projection line in a searched orientation by rotation about the relevant axis. In the case of manual operation it is favourable for the C-arm to be balanced for re-orientation. This applies to rotation about the axes 12 and 14 because in the case of unbalance, with the C-arm 6 uncoupled for movement, instabilities might occur. To obviate this, the C-arm 6 the X-ray source 2 and the X-ray image intensifier 4 can be uncoupled only in a zero reference position, the gravity point coinciding substantially with the isocentre and with the point of intersection of the axes of rotation 12 and 14, and hence being on each of the axes 12 and 14. Rotation about the two axes may then be carried out against only the frictional forces. In many cases it will be desirable for an optimum image formation that the X-ray detector, in this case the X-ray image intensifier 4, be positioned as closely as possible near the object during the image formation. For this purpose, the X-ray image intensifier 4 is mounted so as to be movable in the direction of the radiation vector. For re-orientation it may then be moved, for example, first to the zero reference position, i.e. the balanced position, and then the re-orientation may be carried out. For manual operation depression of an uncoupling button, for example, will be permissible only in the zero reference position. For balancing in a zero reference position it may be necessary to add, for example, to the X-ray source 2 a load 52, for example, a block of lead.

Although the invention has been described mainly hereinbefore with reference to the ceiling C-arm construction shown, the invention is by no means restricted thereto. It will be obvious that the supporting beam 18 may also a connected to the floor or to be supporting plate coupled to the floor, so that an apparatus rigidly connected to the floor or a movable apparatus is realised. The three axes of rotation 12, 14 and 20 may also be realised by means of a construction of rods, for example, modified embodiments of constructions as shown in U.S. No. 3,892,967. Such an apparatus may be constructed so that three independent axes of rotation, if desired are also oriented isocentrical. Measuring and recording devices for mutual angular orientations or monitor image orientation may be provided.

What is claimed is:

1. An X-ray examination apparatus comprising an X-ray source and an X-ray detector which are spaced a given distance diametrically with respect to each other and are collectively rotatable about three axes relative to a table which can be moved between the X-ray source and the X-ray detector, which axes are mutually perpendicular, intersecting substantially in a common point and which define a first system of coordinates and in which apparatus means are incorporated for determining the position of a radiation vector along a central X-ray beam which connects the X-ray source and the X-ray detector, of which radiation vector a first reference coordinate system is determined corresponding to the axes of the first system of coordinates, characterized in that computing means are also incorporated for determining the position of the radiation vector with respect to a second reference coordinate system defined by a set of axes corresponding to said three axes and displaced with respect to the first system of coordinates.

2. An X-ray examination apparatus as claimed in claim 1, characterized in that for all examinations an axis orientation optimized for diagnostic image display can be adjusted with respect to an object to be examined.

3. An X-ray examination apparatus as claimed in claim 1, characterized in that a major axis of the apparatus can always be adjusted so as to coincide with a major axis of an object to be examined.

4. An X-ray examination apparatus as claimed in claim 1, characterized in that the computing means produce a previously adjusted radiographic program with a minimum of rotations.

5. An X-ray examination apparatus as claimed in claim 1, characterized in that axes of rotation comprise angle measuring devices and signals of the said measuring devices can be applied to a central control device (44).

6. An X-ray examination apparatus as claimed in claim 1, characterized in that light views are added to a detection device to form an image corresponding to a given radiation vector orientation.

7. An X-ray examination apparatus as claimed in claim 1, characterized in that an angle encoder is added to an axis of rotation to measure and display angular positions occupied by the said axis.

8. An X-ray examination apparatus as claimed in claim 1, characterized in that an X-ray image intensifier tube can be moved in the direction of the radiation vector while maintaining a balanced C-arm.

9. An X-ray examination apparatus as claimed in claim 1, characterized in that it comprises a C-arm in which an X-ray source and an X-ray detector are mounted so that the C-arm can be rotated over at least twice 90° through a C-arm base.

10. An X-ray examination apparatus of claim 1 wherein said apparatus includes imaging means for producing an image display of an object being irradiated by X-rays from said source, said computing means being arranged to produce a fixed orientation of the image display with respect to a reference axis in the object.

11. The apparatus of claim 1 wherein said computing means include means for determining the position of the radiation vector with respect to said second reference coordinate system which is rotated with respect to the first system of coordinates.

* * * * *